(12) United States Patent
Mueller et al.

(10) Patent No.: US 9,700,645 B2
(45) Date of Patent: Jul. 11, 2017

(54) TWO-PHASE EXHAUSTION INDICATOR FOR FRAGRANCE RELEASE SYSTEMS

(71) Applicant: SYMRISE AG, Holzminden (DE)

(72) Inventors: Dirk Mueller, Dassel (DE); Joern Wiedemann, Holzminden (DE); Jennifer Rube, Hoexter (DE)

(73) Assignee: SYMRISE AG, Holzminden (DE)

( * ) Notice: Subject to any disclaimer, the term of this patent is extended or adjusted under 35 U.S.C. 154(b) by 80 days.

(21) Appl. No.: 14/891,231

(22) PCT Filed: May 9, 2014

(86) PCT No.: PCT/EP2014/059522
§ 371 (c)(1),
(2) Date: Nov. 13, 2015

(87) PCT Pub. No.: WO2014/184100
PCT Pub. Date: Nov. 20, 2014

(65) Prior Publication Data
US 2016/0114068 A1    Apr. 28, 2016

(30) Foreign Application Priority Data

May 14, 2013 (EP) .................................. 13167589

(51) Int. Cl.
| | | |
|---|---|---|
| *A61L 9/12* | (2006.01) | |
| *A61L 9/012* | (2006.01) | |
| *G01N 21/78* | (2006.01) | |

(52) U.S. Cl.
CPC .............. *A61L 9/012* (2013.01); *G01N 21/78* (2013.01)

(58) Field of Classification Search
CPC ................................... C11B 9/00; A61L 9/012
See application file for complete search history.

(56) References Cited

U.S. PATENT DOCUMENTS

| | | | | |
|---|---|---|---|---|
| 4,128,508 A | * | 12/1978 | Munden ................. | G01N 31/22 424/76.4 |
| 5,190,915 A | * | 3/1993 | Behan .................. | A61K 8/0295 424/49 |
| 8,998,103 B2 | | 4/2015 | Meier et al. | |
| 2010/0166604 A1 | * | 7/2010 | Lim ..................... | G01N 21/253 422/400 |
| 2012/0193443 A1 | * | 8/2012 | Meier .................... | A61L 9/127 239/44 |

FOREIGN PATENT DOCUMENTS

| | | |
|---|---|---|
| DE | 102009058078 | 7/2010 |
| DE | 102009045482 | 4/2011 |
| EP | 0309173 | 3/1989 |
| GB | 2444702 | 6/2008 |
| WO | 03031966 | 4/2003 |
| WO | 2004087225 | 10/2004 |
| WO | 2009044363 | 4/2009 |
| WO | 2011042222 | 4/2011 |

OTHER PUBLICATIONS

International Search Report for PCT/EP2014/09522, English translation attached to original, Both completed by the European Patent Office on Aug. 11, 2014, All together 5 pages.

\* cited by examiner

*Primary Examiner* — Lanee Reuther
(74) *Attorney, Agent, or Firm* — Brooks Kushman P.C.

(57) ABSTRACT

A two-phase system containing at least one solvatochromic dye, water, at least one fragrance, and at least one solvent. Wherein the two-phase system includes liquid phases layered one on top of the other. The inventive compositions can be used as exhaustion indicators for fragrance release systems.

9 Claims, No Drawings

TWO-PHASE EXHAUSTION INDICATOR FOR FRAGRANCE RELEASE SYSTEMS

CROSS-REFERENCE TO RELATED APPLICATION

This application is the U.S. national phase of PCT Application No. PCT/EP2014/059522 filed on May 9, 2014, which claims priority to EP Patent Application No. 13167589.4 filed on May 14, 2013, the disclosures of which are incorporated in their entirety by reference herein.

FIELD OF THE INVENTION

The invention is in the field of fragrances and relates to specific mixtures comprising fragrances and dyes, to a method of indicating the expiration of fragrancing systems, and to a device comprising said mixtures.

PRIOR ART

Rooms are fragranced and refreshed by using not only spray systems, but also especially evaporation systems. Generally, said evaporation systems consist of carrier materials, very simple containers and highly specific containers containing auxiliary agents, from which the fragrances are delivered into the room air. For a long time, there have been efforts to provide the user with a visual signal to indicate that the supply of fragrances has been consumed.

U.S. Pat. No. 4,128,508 achieves this object by means of an indicator system comprising a pH indicator and a slow-evaporating acid or base. By means of the change in pH of the fragrance mixture, the altered color of the pH indicator indicates expiration. WO 03/031966 A1 describes a system comprising volatile dyes. The evaporation of the volatile dye brings about a color change which signals the consumption of the fragrances. A disadvantage of both systems is that the color change is not caused by the fragrances themselves, but by auxiliary agents. This means that achieving a reliable expiration indicator requires selecting the fragrances such that they evaporate just as rapidly as the auxiliary agents. This makes it impossible or at least considerably difficult to prepare a creative and complex scent.

GB 2444702 A discloses nonaqueous mixtures comprising halochromes, fragrances, nonvolatile acids or bases, and highly polar, low-volatile solvents.

DE 102009058078 discloses a moth protection sack comprising, inter alia, the fragrance lavandin abrialis oil, the solvent dipropylene glycol and the solvatochromic dye Nile blue.

EP0309173 discloses expiration indicators comprising solvent, indicator dye, preferably selected from the group of the xanthenes, and fragrances.

WO2009044363 discloses compositions for application to keratinous materials, wherein the compositions comprise a holographic pigment. A disadvantage of pigments is their insolubility, and such compositions, if used for example in liquids of low viscosity, therefore have a tendency to separate and to consequently give an unevenly colored product.

WO2011042222 discloses fragrance delivery systems having an activation and/or consumption indicator comprising optionally solvatochromic dyes.

Known expiration indicators for fragrance systems frequently have substantial disadvantages. Firstly, the evaporation of the fragrances leads to the concentration of the remaining dye, and so the color intensity of the fragrance composition gradually increases. Consequently, the user cannot very readily distinguish between the color change and the color intensification and cannot especially easily identify the actual expiration.

Frequently, the color change takes place only very gradually over a long period from a few weeks to months. Consequently, the consumer gets accustomed to the daily minimal color changes and only perceives the full extent of the color change with difficulty. Even if the original shade and the expiration shade are very far apart from one another, the result of this accustoming effect is that the actual expiration cannot be especially easily identified.

Furthermore, the volume or the surface area of the dye solution decreases as a result of the evaporation of the fragrances. Consequently, at expiration, there is frequently only a tiny area or a tiny volume of the indicator dye. For this reason too, the actual expiration cannot be especially easily identified.

OBJECT OF THE INVENTION

It is therefore primarily an object of the present invention to provide fragrance systems with expiration indicator which avoid the prior art disadvantages described at the beginning. The systems are notable for an especially easy identifiability of expiration; more particularly, they do not exhibit a gradual color intensification upon evaporation of the fragrances, they have a sudden color change at expiration and/or they have at the end of their usage life a sufficiently large indicator of expiration. Furthermore, the fragrance system can indicate to the user that a delivery of fragrance to the surroundings is taking place.

DESCRIPTION OF THE INVENTION

The object is achieved by a two-phase system comprising
a. at least one solvatochromic dye,
b. water,
c. at least one fragrance,
d. and optionally at least one solvent,
characterized in that the two-phase system consists of liquid phases layered one on top of the other, the phases being immiscible with one another and having a common phase boundary.

The two-phase system preferably comprises a lower phase comprising water and an upper phase comprising at least one fragrance (component c).

The solvatochromic dyes (component a) have at least a minimal solubility in both phases and should preferably especially strongly accumulate in one of the two phases, the concentration of the dye in the high-dye phase being preferably at least 10-fold, particularly preferably 100-fold and very particularly preferably 1000-fold higher than in the low-dye phase (determined using UV/Vis spectrometry at 20° C.). In principle, it is possible for the dye to be especially strongly accumulated in the upper phase or in the lower phase; preference is given to those two-phase systems in which the dye is especially strongly accumulated in the upper phase. The fragrances can also be especially strongly accumulated in either the upper phase or the lower phase, the concentration of the fragrances in the high-fragrance phase being preferably at least 10-fold, particularly preferably 100-fold and very particularly preferably 1000-fold higher than in the low-fragrance phase. Particular preference is given to those systems in which the fragrances together with the solvatochromic dyes (component a) are strongly accumulated in the upper phase.

The high accumulation of solvatochromic dyes (component a) in one of the two phases results in this high-dye phase appearing very intensely colored and the other (low-dye) phase appearing virtually colorless or merely negligibly colored. Surprisingly, during evaporation of the fragrances, there is initially no pronounced transfer of the solvatochromic dyes (component a) to the low-dye phase. Only upon virtually complete evaporation of the fragrances from the high-dye phase is there an appreciable transfer of the solvatochromic dyes (component a) into the phase that was originally low in dye. The phase that was originally low in dye is now, at expiration, distinctly colored, with the color change taking place suddenly. It is now possible for the user to identify expiration very clearly from the increase in color intensity of the phase that was originally low in dye.

The color changes in the phase that was originally high in dye, more particularly the color change within the region of visible light and the color intensification, signal to the user that the system is still delivering fragrances into the surroundings. This aspect is likewise important for signaling to the user that the fragrance delivery system is still active. Furthermore, the user can receive the benefit of a gradual color change even during the long usage time.

The two-phase system according to the invention is not an emulsion. Although emulsions are inhomogeneous two-phase systems at the microscopic level, they appear homogeneous when considered macroscopically and outwardly, and so the effects according to the invention for the user are not exhibited with respect to emulsions.

In the context of the present invention, solvatochromic dyes (component a) are those dyes in which the effect of solvatochromism occurs. Solvatochromism is defined by Rompp Online (http://www.roempp.com/) as "a change in light absorption of a dissolved substance (a chromophore) depending on the solvent". Solvatochromic dyes to be used with preference are selected from the group which is formed by merocyanines, red pyrazolone dyes, azomethine dyes, indoaniline dyes, pyridinium N-phenoxide betaines, Nile red, Reichardt dye, Nile blue, dimethylaminobenzaldehyde, 4-[2-N-substituted-1,4-hydropyridin-4-ylidene)ethylidene] cyclohexa-2,5-dien-1-one, 1-(4-hydroxyphenol)-2,4,6-triphenylpyridinium, 5-dimethylamino-5'-nitro-2,2'-bithiophene and mixtures thereof. The solvatochromic dye that is particularly preferred is Nile red.

The solvatochromic dyes are used in the two-phase systems according to the invention preferably to an extent of from 0.0001 to 0.1% by weight and particularly preferably to an extent of from 0.001 to 0.01% by weight, based in each case on the sum total of components a, b, c and d.

Preferably, the water fraction (component b) in the two-phase systems according to the invention is between 0.5 and 70% by weight, preferably from 20 to 60% by weight and particularly preferably 30-55% by weight, based on the total mass of components a, b, c and d. The water fraction is especially necessary in the two-phase systems according to the invention in order to provide a second phase for the inventive effects described further above and/or to provide a sufficiently large indicator area/a sufficiently large indicator volume at expiration.

In the context of the invention, fragrances (component c) are especially those fragrances which create a pleasant odor impression. Preference is given to fragrances from group c1 which is formed by aldehydes, esters, ketals and mixtures thereof. Particularly preferably, the fraction of group c1, based on the total mass of components c, is at least 20% by weight. The selection of these fragrances contributes to an especially sudden color shift at expiration.

Solvents (component d) are especially solvents suitable for fragrances, selected preferably from the group of the alcohols and particularly preferably from the group which is formed by ethanol, propanol, butanol, isopropyl alcohol, propanediol, butanediol, pentanediol, hexanediol, phenylethyl alcohol, 3,3-methylmethoxybutanol, Solutol, dipropylene glycol monomethyl ether, tripropylene glycol monomethyl ether, propylene glycol phenyl ether, phenoxyethyl alcohol, propylene glycol, dipropylene glycol, triethylene glycol, glycerol, 2-methyl-1,3-propanediol and mixtures thereof. The solvents may be required in order to establish at least a slight solubility of the solvatochromic dyes (component a) in the low-dye phase and to ensure a color shift to the low-dye phase at the point of expiration. In addition, it is thereby possible to set the initial color of the low-dye phase between colorless and light pastel shades.

The two-phase systems can optionally comprise stabilizing agents in order to further increase (light) stability. According to the invention, stabilizing agents are preferably understood to mean light protection agents, antioxidants, preservatives and emulsifiers.

The two-phase systems according to the invention can optionally comprise further dyes from the group of the nonsolvatochromic dyes in order to set other color shades or the like.

In a further preferred form of the invention, the two-phase systems are free from emulsifiers. Operating filling systems for liquids at high throughput rates is striven for and operations are therefore carried out at high filling speeds. This is associated with a strong mixing of the components and there is the risk of the undesired formation of emulsion. A formation of emulsion is avoided by the absence of emulsifiers.

The invention also provides a method of indicating the expiration of fragrance systems, in which the components according to the invention:
 a. at least one solvatochromic dye,
 b. water,
 c. at least one fragrance,
 d. and optionally at least one solvent,
are contacted such that a two-phase system consisting of liquid phases layered one on top of the other is formed and said system is exposed to the air, with a sudden color change taking place in the two-phase system as soon as the fragrances have been almost completely delivered into the air. Preferably, a gradual color change and a sudden color change take place in the two-phase system.

According to the invention, a sudden color change is preferably understood to mean a color change within one week, preferably within 4 days and particularly preferably within one day.

According to the invention, an almost complete delivery of fragrances is preferably understood to mean a delivery of more than 80% by weight, and particularly preferably of more than 90% by weight, of the original mass of the fragrances into the air.

Preferably, the color change takes place between the two phases in such a way that the dye concentration in the phase that was originally low in dye suddenly rises after at least 90% by weight of the fragrances have been delivered into the air and the color of the phase that was originally low in dye is, after the color change, of a different color to the high-dye phase.

In a further preferred embodiment of the invention, the mixture according to the invention is present in a container which has a semipermeable membrane or consists of a semipermeable membrane. In a preferred embodiment, the semipermeable membrane consists of polyethylene. At least part of the container should be light-permeable within the region of visible light. Further forms in which the mixtures according to the invention can be used are air fresheners for rooms, dishwashers, clothes dryers, toilets and also fragrance lamps with transparent oil reservoir. Optionally, the container can comprise a screen for one of the two phases; in this case, the cover should be effected such that the phase cannot be seen by an observer. Preferably, the container comprises a screen for the low-dye phase. In this case, it is especially easy for the user to determine expiration.

The invention also provides a preparation process for producing the two-phase systems according to the invention, comprising the steps:
I. provision of a phase I comprising water (component b)
II. provision of a phase II comprising fragrances (component c) and at least one solvatochromic dye (component a) and
III. layering phase II on top of phase I.

The solvents (optional component d) are preferably added to phase II in step II. In step II, the solvatochromic dye (component a) is mixed with the fragrances and optionally the solvents in order to produce a solution of the dye.

Lastly, the invention also provides for the use of the two-phase systems according to the invention for indicating the expiration of fragrance delivery systems.

EXAMPLES

Example 1

A two-phase fragrance composition was produced from the following components:

|  | Quantity weighed (g) | Component |
| --- | --- | --- |
| Phase I | 25.9998 | Water |
| Phase II | 59.2000 | Fragrances (mixture of aldehydes, esters and ketals) |
|  | 14.8000 | Dipropylene glycol |
|  | 0.0002 | Nile red |

The water was initially charged into a first beaker. In a second beaker, the fragrances, the dipropylene glycol and the Nile red were stirred together until the Nile red had dissolved.

The content of the second beaker was carefully layered on top of the water phase. The beaker was openly exposed to the air in a fume hood. Initially, the upper phase (phase II) is pink in color and the lower phase (phase I) is colorless. With increasing evaporation of the fragrances and the dipropylene glycol, the color intensity of the pink shade gradually increases and the shade gradually shifts in the direction of the color red. The evaporation process is continued until only a small ring of the upper phase remains. This ring appears, then, dark red-violet. The lower phase remains colorless for a very long time and its volume remains virtually constant. Only with the onset of the formation of the ring of the upper phase does the colorless lower phase, at first, suddenly change to a light violet shade and, shortly thereafter, suddenly change to a deep blue shade. At the upper phase, the observer can see that the shade is gradually changing and that the system is delivering fragrances. At the lower phase, the observer sees a sudden color change and can identify expiration of the fragrance delivery system therefrom.

Example 2

Portions of the two-phase system according to example 1 are produced (6 g in each case) and filled into clear and transparent polyethylene beakers. The opening of the polyethylene beakers is sealed with a polyethylene membrane.

The sealed beakers are placed in a room at a temperature of 20° C. and the mass fraction of the evaporated fragrances over time is determined by weighing the sealed beakers. The following underlying formula was used:

$$\frac{\text{Mass fraction of}}{\text{evaporated fragrances}} = 100 - \frac{\text{Mass at time } t * 100\%}{\text{Mass at time } t = 0}$$

| Time of experiment (t) in hours | Mass fraction of evaporated fragrances | Color of upper phase II | Color of lower phase I |
| --- | --- | --- | --- |
| 0 | 0 | Light pink | Colorless |
| 48 | 14.6 | Light pink | Colorless |
| 96 | 39.7 | Pink | Colorless |
| 144 | 58.7 | Pink | Colorless |
| 192 | 73.2 | Dark pink | Colorless |
| 240 | 83.7 | Red ring | Violet |
| 384 | 93.0 | Red-violet ring | Dark blue-violet |

The experimental results show that a sudden color change occurs in the lower phase after the overwhelming portion of the fragrances has been delivered into the surroundings. Said change is very clear and can indicate expiration to the end user with a very large signal effect.

If, at the start of the experiment, the level of the lower phase I in the beaker is additionally marked, it is ascertained at the end of the experiment that said level has not changed until the end of the experiment. Consequently, a large indicator is provided from which expiration can be read.

Comparative Example 3

Example 3 is repeated, involving adding only 6 g of phase II from example 1 to the polyethylene beakers, i.e., phase I is not present in this experiment. The single-phase system prepared for comparative purposes changes the shade from light pink, via pink, dark pink, red and red-violet. Because of the gradual color shift between very similar tones, the end user can identify expiration here only with great imprecision. At the end of the experiment, only a small red-violet ring remains at the bottom of the beaker. In this comparative case, the size of the indicator is distinctly smaller than in the inventive example 2.

The invention claimed is:
1. A two-phase system comprising:
a. at least one solvatochromic dye,
b. water,
c. at least one fragrance, and
d. at least one solvent,
wherein the two-phase system includes two liquid phases layered one on top of the other, with the at least one fragrance and the at least one solvatochromic dye are in the same layer.
2. The two-phase system as claimed in claim 1, wherein the at least one solvatochromic dye is selected from the group consisting of merocyanines, red pyrazolone dyes, azomethine dyes, indoaniline dyes, pyridinium N-phenoxide betaines, Nile red, Reichardt dye, dimethylaminobenzaldehyde, 4-[2-N-substituted-1,4-hydropyridin-4-ylidene)ethylidene]-cyclohexa-2,5-dien-1-one, 1-(4-hydroxyphenol)-2,4,6-triphenylpyridinium, 5-dimethylamino-5'-nitro-2,2'-bithiophene and mixtures thereof.

3. The two-phase system as claimed in claim 1, wherein the at least one solvatochromic dye is Nile red.

4. The two-phase system as claimed in claim 1, wherein the water makes up between 0.5 and 70% by weight of the two-phase system, based on the total mass of components a, b, c and d.

5. The two-phase system as claimed in claim 1, wherein the at least one solvent is between 0 and 20% by weight of the total mass of components a, b, c and d.

6. The two-phase system as claimed in claim 1, wherein the at least one fragrance is selected from group c1 consisting of aldehydes, esters, ketals and mixtures thereof.

7. The two-phase system as claimed in claim 1, wherein the at least one solvent is selected from the group consisting of ethanol, propanol, butanol, isopropyl alcohol, propanediol, butanediol, pentanediol, hexanediol, phenylethyl alcohol, 3,3-methylmethoxybutanol, Solutol, dipropylene glycol monomethyl ether, tripropylene glycol monomethyl ether, propylene glycol phenyl ether, phenoxyethyl alcohol, propylene glycol, dipropylene glycol, triethylene glycol, glycerol, 2-methyl-1,3-propanediol and mixtures thereof.

8. The two-phase system as claimed in claim 1, wherein the two-phase system is free from emulsifiers.

9. A light-permeable container with a closure made of a semipermeable membrane and/or a screen further comprising the two-phase system as claimed in claim 1.

* * * * *